(12) United States Patent
Kim et al.

(10) Patent No.: US 11,484,495 B2
(45) Date of Patent: Nov. 1, 2022

(54) SUSTAINED-RELEASE INJECTABLE COMPOSITION COMPRISING FINASTERIDE

(71) Applicant: INVENTAGE LAB INC., Seongnam-si (KR)

(72) Inventors: Ju Hee Kim, Seongnam-si (KR); Se Yeon Kim, Suwon-Si (KR)

(73) Assignee: INVENTAGE LAB INC., Seongnam-si (KR)

( * ) Notice: Subject to any disclaimer, the term of this patent is extended or adjusted under 35 U.S.C. 154(b) by 0 days.

(21) Appl. No.: 17/129,028

(22) Filed: Dec. 21, 2020

(65) Prior Publication Data
US 2021/0186864 A1    Jun. 24, 2021

(30) Foreign Application Priority Data

Dec. 23, 2019 (KR) .......................... 10-2019-0172595

(51) Int. Cl.
| | | |
|---|---|---|
| *A61K 9/00* | (2006.01) | |
| *A61K 9/10* | (2006.01) | |
| *A61K 9/16* | (2006.01) | |
| *A61K 31/58* | (2006.01) | |
| *A61K 47/02* | (2006.01) | |
| *A61K 47/26* | (2006.01) | |

(52) U.S. Cl.
CPC .............. *A61K 9/0019* (2013.01); *A61K 9/10* (2013.01); *A61K 9/1647* (2013.01); *A61K 31/58* (2013.01); *A61K 47/02* (2013.01); *A61K 47/26* (2013.01)

(58) Field of Classification Search
CPC ...... A61K 9/0019; A61K 9/10; A61K 9/1647; A61K 31/58; A61K 47/02; A61K 47/26; A61K 47/38; A61K 9/0021; A61K 47/30; A61P 17/14; A61P 13/08
See application file for complete search history.

(56) References Cited

U.S. PATENT DOCUMENTS 6,277,391 B1    8/2001    Seo et al.

FOREIGN PATENT DOCUMENTS

| CN | 107028893 A | 8/2017 | |
|---|---|---|---|
| JP | 2019534900 A | 12/2019 | |
| KR | 2016002411 A | 1/2016 | |
| KR | 20190019821 A | 2/2019 | |
| KR | 20200099901 A | 8/2020 | |
| WO | WO-2018070940 A1 * | 4/2018 | ........... A61K 9/0019 |
| WO | WO2020166820 A1 | 8/2020 | |

OTHER PUBLICATIONS

Kazumichi et al. (JPH08157370A Machine English Translation) (Year: 1996).*
European Search Report of EP20 21 6356, dated May 11, 2021.
Ju Hee Kim et al., Development of finasteride polymer microspheres for systemic application in androgenic alopecia, International Journal of Molecular Medicine, Mar. 27, 2019, pp. 2409-2419, vol. 43, Demetrios Spandidos, Athens, Greece.
Osama A. Ahmed et al., Optimisation of microstructured biodegradable finasteride formulation for depot parenteral application, Journal of Microencapsulation, Feb. 15, 2016, pp. 229-238, vol. 33, No. 2, Taylor & Francis Group, London, United Kingdom.

* cited by examiner

*Primary Examiner* — Robert A Wax
*Assistant Examiner* — Quanglong N Truong
(74) *Attorney, Agent, or Firm* — STIP Law Group, LLC

(57) ABSTRACT

The present disclosure relates to a sustained-release injectable composition comprising finasteride, and when the composition is injected as an injection formulation, it is possible to maintain a constant blood concentration for a long time without initial over-release in terms of the degree of release of finasteride, and when the composition is administrated by subcutaneous injection, it is possible to maintain the effect of treating hair loss and benign prostatic hyperplasia continuously for 1 to 3 months.

7 Claims, 7 Drawing Sheets

SUSTAINED-RELEASE INJECTABLE COMPOSITION COMPRISING FINASTERIDE

CROSS-REFERENCE TO RELATED APPLICATIONS

This application claims the priority of the Korean Patent Applications NO 10-2019-0172595 filed on Dec. 23, 2019 in the Korean Intellectual Property Office, the disclosure of which is incorporated herein by reference.

TECHNICAL FIELD

The present disclosure relates to a sustained-release injectable composition comprising finasteride, and more particularly, to a sustained-release injectable composition comprising finasteride capable of maintaining the effect of drug administration of finasteride for a long time when injected into the body as an injection formulation.

BACKGROUND ART

Agents for treating male-type hair loss being currently used in Korea include finasteride and dutasteride as oral agents. These agents for treating hair loss block 5-α-reductase inhibitors, wherein the agents serve to convert testosterone into dihydrotestosterone (DHT), to inhibit the production of DHT, a powerful male hormone and, through this inhibition, to inhibit the contraction of the hair roots caused by DHT in the scalp, thereby treating androgenic hair loss.

5-α-reductase inhibitors can be divided into Type 1 and Type 2, wherein Type 1 is distributed in the scalp and sebaceous glands, and Type 2 is distributed in the scalp and prostate. Finasteride blocks only Type 2 of the 5-α-reductase inhibitors, but dutasteride blocks both Type 1 and Type 2. This mechanism is known to make dutasteride having a stronger DHT inhibitory effect, than finasteride. However, based on the first one (1) year of administration, the incidence of side effects of dutasteride was higher, and finasteride has been currently used most widely as an agent for treating hair loss and has advantages over dutasteride in terms of safety in that it is the only approved drug by the FDA.

Existing oral agents for treating hair loss, such as those disclosed in Korean Patent Publication No. 10-2016-0002411, have a problem in that it is necessary to take the drug every day for 3 months or more to observe the therapeutic effect, and when the drug administration is stopped, the drug efficacy decreases and the hair returns to its previous state. Therefore, there is a problem in existing oral agents that in order to maintain the effect of treating hair loss by sustaining the drug efficacy, it is necessary to continuously take the drug at a certain time every day.

An agent for treating hair loss, such as dutasteride and finasteride is associated with male hormones and is thus designated as contraindicated drugs for woman of childbearing age or pregnant woman, and the exposure of a woman of childbearing age or a pregnant woman to the agent for treating hair loss may cause abnormalities in the external genitalia of the male fetus, which may lead to birth defects. Thus, the agent for treating hair loss should be taken with care in storing or handling. In addition, since the drug may also be absorbed through the skin and affect the fetus, the drug has a problem in that the drug should not be touched, and the person taking the drug who lives with a woman of childbearing age or a pregnant woman needed to be handled with particular care.

That is, conventional agents for treating hair loss, such as dutasteride and finasteride are provided only in formulations for oral administration.

It is suggested that the effect of treating hair loss will occur only when the user receives a prescription for the drug at the hospital, brings the drug home, keeps it and takes it continuously at a certain time every day.

Such a usage was problematic in that it made it inconvenient to use an agent for treating hair loss for a woman of childbearing age or a pregnant woman whose expose to the agent is contraindicated.

Therefore, there is urgent need to develop an agent for treating hair loss that uses finasteride whose stability is recognized as an agent for treating hair loss, may maintain the effect for 1 month or more by one administration, can maintain the drug efficacy for 1 month or more by one administration, and is easy to store and handle because it can be administered by subcutaneous injection instead of oral formulation.

PRIOR ART DOCUMENTS

Patent Documents (Patent Document 1) KR 10-2016-002411 A1

DISCLOSURE

Technical Problem

An object of the present disclosure is to provide a sustained-release injectable composition comprising finasteride.

Another object of the present disclosure is to provide an injectable composition comprising finasteride capable of maintaining a constant blood concentration for a long time without initial over-release when injected as an injection formulation.

Still another object of the present disclosure is to provide an injectable composition whose convenience in storage and handling is excellent, by providing a dosage form for subcutaneous injection, not an oral formulation, so that a user does not need to store the drug, and the effect of treating hair loss and benign prostatic hyperplasia by finasteride may be exhibited through a mode of direct administration at a hospital.

Yet another object of the present disclosure is to provide a composition for subcutaneous injection capable of maintaining a therapeutic effect for hair loss and treatment for benign prostatic hyperplasia continuously for 1 to 3 months.

Still yet another object of the present disclosure is to provide a sustained-release injectable composition comprising sustained-release particles containing finasteride which is capable of maintaining a constant effective drug concentration by controlling the release of the drug by being prepared to have an average particle diameter of constant micro size, and capable of reducing foreign body sensation and pain when applied to an injectable agent composed of particles of uniform size and administered as an injectable agent to patients, while maintaining the effect of long-term drug administration for a period of 1 to 3 months.

Technical Solution

To achieve the above object, a sustained-release injectable composition comprising finasteride according to an embodiment of the present disclosure is a sustained-release injectable composition comprising finasteride, the sustained-release injectable composition injected into the body continuously releases finasteride, and the released finasteride has a ratio of a maximum blood concentration ($C_{max}$) to an initial blood concentration ($C_{int}$) of 2 to 11.

The maximum blood concentration ($C_{max}$) of finasteride may be 0.3 to 0.5 μg/L for 1 mg of finasteride administered.

The area under the concentration ($AUC_{0-t}$) of finasteride may be 70 to 100 (μg*h/L) for 1 mg of finasteride administered.

The sustained-release injectable composition has no initial over-release problem due to the controlled release rate of the drug, may form a continuous release pattern for 1 to 3 months, and may inhibit the production of DHT and testosterone.

The injectable composition may include a suspending solvent, and the suspending solvent may include an isotonic agent, a suspending agent, and a solvent.

The isotonic agent may be selected from the group consisting of D-mannitol, maltitol, sorbitol, lactitol, xylitol, sodium chloride and a mixture thereof.

The suspending agent may be selected from the group consisting of sodium carboxymethylcellulose, polysorbate 80, starch, starch derivative, polyhydric alcohol, chitosan, chitosan derivative, cellulose, cellulose derivative, collagen, gelatin, hyaluronic acid (HA), alginic acid, algin, pectin, carrageenan, chondroitin, chondroitin, chondroitin sulfate, dextran, dextran sulfate, polylysine, titin, fibrin, agarose, fluran, xanthan gum and a mixture thereof.

In the present disclosure, the term "injection" is to inject a drug solution intradermally, subcutaneously, intramuscularly, intravenously, or intra-arterially using a syringe. Specifically, the injection may be a subcutaneous injection, but is not limited thereto, due to the nature of the pharmaceutical composition of the present disclosure, which exhibits an efficacy of preventing hair loss or promoting hair growth. The syringe may be used without limitation as long as it is a syringe used to administer the composition of the present disclosure subcutaneously as well as a general syringe capable of administering a drug solution through a needle.

The subcutaneous tissue is a portion between muscles and bones under the dermal layer, and has fat cells including a large amount of fat to soften the human body and to form a contour, and can be used as energy. The subcutaneous tissue also means that the arteries and lymph fluid are circulating.

In the present disclosure, an isotonic agent is a compound that is physiologically resistant and imparts adequate tonicity to the formulation in order to prevent the net flow of water across cell membranes in contact with the formulation.

In the present disclosure, administration means the introduction of a predetermined substance into an individual by an appropriate method. In the present disclosure, the composition may be administered to a subcutaneous tissue, due to the nature of preventing hair loss or promoting hair growth by injection into an individual.

Advantageous Effects

According to the sustained-release injectable composition comprising finasteride of the present disclosure, when the composition is injected as an injection formulation, it is possible to maintain a constant blood concentration for a long time without initial over-release in terms of the degree of release of finasteride, and when the composition is administrated by subcutaneous injection, it is possible to maintain the effect of treating hair loss continuously for 1 to 3 months.

The injectable composition controls the release of the drug so that the effective drug concentration can be maintained at a constant level, and may reduce the foreign body sensation and pain when administered to a patient as an injectable agent.

Also, the present disclosure is provided an injectable composition having excellent storage and ease of handling by providing a dosage form for subcutaneous injection, not an oral formulation, so that the user does not need to store the drug, and the effect of treating hair loss and treating benign prostatic hyperplasia by finasteride may be exhibited through a mode administered directly at a hospital.

BEST MODE

Figure 1:
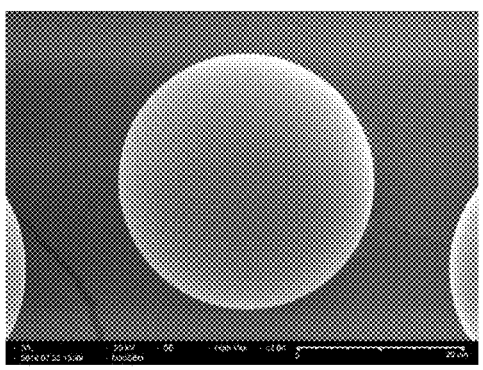
FIG. 1 is an SEM photograph of sustained-release particles according to an embodiment of the present disclosure.

Hereinafter, embodiments of the present disclosures will be described in detail so as to be easily carried out by those skilled in the art to which the present disclosure pertains. However, the present disclosures may be implemented in various different forms and is not limited to the embodiments described herein.

In general, there was a problem in that finasteride is composed of a solid oral formulation for oral administration, so that the user has to take the finasteride formulation at a certain time every day, and the drug has to be stored at home for an administration.

As explained previously, finasteride is associated with male hormones and is thus designated as contraindicated drugs for woman of childbearing age or pregnant woman, and the exposure of a woman of childbearing age or a pregnant woman to the agent for treating hair loss may cause abnormalities in the external genitalia of the male fetus, which may lead to birth defects. Thus, there was an inconvenience of taking the agent for treating hair loss with care in storing or handling.

In addition, in the case of taking a solid oral formulation, there may be a problem in that the blood concentration of finasteride remains high when solid oral formulation is taken every day.

That is, in the case of finasteride taken as an oral formulation, the maximum blood concentration ($C_{max}$) is up to 46.30 μg/L, and when taken daily, finasteride continues to maintain a high blood concentration.

In order to show the drug effect from taking finasteride, the user may have an exposure problem of excessive finasteride in situations where it is not necessary to have a maximum blood concentration value equivalent to that of an oral formulation.

Therefore, the present disclosure relates to the sustained-release particles comprising finasteride, which can be used as injectable formulations, not oral formulation.

Specifically, the sustained-release particles comprise finasteride and a biodegradable polymer, have a spherical shape uniformly comprising finasteride and a biodegradable polymer, and have an average diameter of 35 to 55 μm.

The sustained-release particles comprise a biodegradable polymer and finasteride, wherein a composition in which the biodegradable polymer and finasteride are uniformly mixed, not in a capsule form formulation, is prepared from the sustained-release particles in a complete spherical shape, and is characterized in that finasteride is evenly distributed in the sustained-release particles.

Thus, when the composition for subcutaneous injection of the present disclosure is injected into the body, the sustained-release particles themselves are administered into the body, and as the biodegradable polymers constituting the sustained-release particles are decomposed over time, finasteride, which has been evenly distributed, is released into the body.

As described above, finasteride released into the body may exhibit an effect of preventing hair loss or promoting hair growth.

In addition, the composition of the present disclosure may be used as an injection formulation, which can solve storage and handling problems when provided as a solid oral formulation.

The sustained-release particles have an average diameter of 35 to 55 and the standard deviation of the average diameter is 3.0 to 5.5.

The present disclosure relates to the sustained-release particles prepared by a method for preparing sustained-release particles to be described later, and is characterized in that, as described above, a biodegradable polymer and finasteride are evenly distributed, and the prepared sustained-release particles have an average diameter of 35 to 55 and the standard deviation of the average diameter is 3.0 to 5.5.

That is, even though micro-sized particles are prepared, the standard deviation is only 3.0 to 5.5, and thus particles of almost the same size may be prepared.

In the case of the solvent evaporation method, which is commonly known as a method of preparing sustained-release particles using a polymer, the diameter range of the prepared particles varies, so that in relation with the preparation of particles having an average diameter of 35 to 55 μm as in the present disclosure, there is a problem in that the production yield is too low in that the sustained-release particles are prepared and need to be used after classifying and removing too small or too large particles.

On the other hand, the sustained-release particles of the present disclosure have an average diameter of 35 to 55 μm and a standard deviation of only 3.0 to 5.5, so that the sustained-release particles of almost the same size may be prepared in large quantities and thus have excellent production yield.

If the average diameter of the particles is 35 μm or less, small sustained-release particles with a diameter of 20 μm or less are likely to be prepared, and have an increased possibility of being engulfed by macrophages after injection into the body, thereby affecting the release of effective drug and absorption in vivo. In addition, if the average diameter of the particles exceeds 55 μm, foreign body sensation and pain may be increased when the injectable agent is administered, and the particle size distribution of the prepared particles may be increased, thereby making it difficult to prepare sustained-release particles having a uniform particle size.

The sustained-release particles of the present disclosure have a specific surface area of $1.40 \times 10^{-1}$ m$^2$/g~$1.50 \times 10^{-1}$ m$^2$/g, and the maximum blood concentration ($C_{max}$) of finasteride is 0.9 to 10.0 μg/L after injection into the body.

In addition, the standard deviation of the maximum blood concentration ($C_{max}$) is 0.5 to 5.

The sustained-release particles according to an embodiment of the present disclosure are characterized in that they have a complete spherical shape and have a spherical surface evenly formed, wherein the specific surface area is $1.40 \times 10^{-1}$ m$^2$/g~$1.50 \times 10^{-1}$ m$^2$/g.

As the sustained-release particles have the specific surface area value as described above, when the sustained-release particles of the present disclosure are injected, the maximum blood concentration ($C_{max}$) may be 0.9 to 10.0 μg/L.

In the case of finasteride, which is generally taken as an oral formulation, the effective concentration is reached 1 to 2 hours after administration, and it is guided that it is necessary to take the drug for 3 days based on a healthy adult male to maintain a certain concentration due to the half-life of the drug.

That is, finasteride, which is taken as an oral formulation, exhibits a maximum blood concentration 1 to 2 hours after administration, and at this time, the maximum blood concentration ($C_{max}$) is 42.87 μg/L, which represents a high value, while the sustained-release particles of the present disclosure may exhibit a relatively very low maximum blood concentration value even after injection into a body.

The oral formulation exhibits a high level in the maximum blood concentration by administration, but the half-life is relatively short, so that it is necessary to take the drug daily to maintain the effective concentration, and the blood concentration value is high after taking the oral formulation, so that in fact, it is necessary to take the drug above the blood concentration that shows the therapeutic effect by taking finasteride.

On the other hand, the sustained-release particles of the present disclosure have a maximum blood concentration of 0.9 to 10.0 μg/L after administration as an injection formulation, which exhibits a therapeutic effect by the administration of finasteride, and at the same time, may relatively lower the occurrence of side effects by administration of finasteride due to a lower blood concentration value than that of the oral formulation However, since the maximum blood concentration value can be varied by the amount of finasteride administered, relative numerical comparison is difficult.

Accordingly, it has been confirmed that considering that finasteride taken in an oral formulation is usually taken at 1 mg, the maximum blood concentration in the oral formulation is 42.87 μg/L.

On the other hand, it was confirmed that the sustained-release particles of the present disclosure showed a low maximum blood concentration value of 0.3 to 0.5 μg/L for 1 mg of finasteride based on the dosage.

Compared to the oral formulation, even though the maximum blood concentration value is very low, the production of DHT and testosterone is inhibited due to the effect of sustained release of finasteride for a long time, thereby showing the effect of preventing hair loss and treating benign prostatic hyperplasia.

In the case of an oral formulation, there is a problem to be taken every day due to the influence of the half-life of finasteride, and thus the maximum blood concentration value is continuously maintained in a high level, whereby side effects may occur.

On the other hand, in the case of the present disclosure, it was confirmed that the very low maximum blood concentration value was shown under the condition of administering 1 mg, the same as the oral formulation, and accordingly, it is possible to minimize the occurrence of side effects, and to minimize the burden on the body caused by the release of finasteride by lowering the blood concentration value.

In addition, the oral formulation exhibits a profile in which the maximum blood concentration value is initially displayed and then the blood concentration value decreases rapidly, while the injectable composition of the present disclosure has a controlled release rate of the drug due to the sustained-release particles, thereby preventing an initial over-release problem, and exhibiting a continuous release pattern for 1 to 3 months.

This sustained-release pattern can be confirmed based on the fact that the ratio of a maximum blood concentration ($C_{max}$) to an initial blood concentration ($C_{int}$) is 2 to 11.

If the initial blood concentration value is smaller than the maximum blood concentration value, it means that initial over-release does not occur. Due to the continuous release pattern, the maximum blood concentration value does not show a large difference from the initial blood concentration value, and maintains a constant range.

The sustained-release particles of the present disclosure have an area under the concentration ($AUC_{0-t}$) of 280 to 2000 μg*h/L after injection into the body.

When the blood concentration curve is confirmed over time, an area is formed under the curve, which is called the area under the time versus drug concentration curve, and is abbreviated as AUC.

AUC is determined by the dose and clearance as follows.

AUC=dose/clearance

The clearance (CLs) is a model-independent parameter, but has a mathematical relationship with clearance rate constant (K) and the volume of distribution (V) as follows.

$CLs = V \times K$

As shown in the Equation, clearance and volume of distribution determine the drug clearance rate.

When the clearance is constant, the AUC is proportional to the dose, so that when the drug dose is doubled, the AUC doubly increases. According to this concept, on the one hand, it is also meant that clearance may be obtained by AUC and dose.

Normally, since the blood concentration according to the dosage and time can be known, the AUC can be obtained, and thus the clearance can be obtained by the following Equation.

Drug clearance=dose/$AUC$

Assuming a one-compartment model and administering a certain dose of a drug, the AUC can be easily obtained as follows.

$AUC$=initial concentration($Co$)/clearance rate constant($K$)

However, in the case of a drug whose natural logarithm value of the drug concentration over time decreases linearly or nonlinearly, the AUC can be obtained by a method called "trapezoidal rule."

The trapezoidal rule is to connect the measured blood concentrations in the vicinity of each neighboring blood by a straight line, considering that the curve of blood concentration over time is connected with several ladders.

Although the upper part of the trapezoid is a curve, a small time interval (the height of the trapezoid) can assume the curve as a straight line, and the resulting error becomes very small, which can be ignored.

In this way, each trapezoidal area is easily calculated and the sum of all trapezoidal areas becomes the total area under the concentration curve.

AUC calculation may be very useful for calculating drug clearance.

When the AUC is calculated by the trapezoidal rule, the blood concentration is not substituted with the natural logarithm value.

To calculate the clearance, the AUC from time 0 to infinity needs to be used. The AUC from time 0 to infinity is also calculated by the trapezoidal rule, which uses the method of adding the calculated area from the last measurement time to infinity to the AUC from time 0 to the time when the last concentration is measured.

It will be meant that a large AUC value indicates a relatively high bioavailability. That is, in the case of injecting sustained-release particles comprising finasteride of the present disclosure, it will be referred to as an index of the absorption amount indicating how much the sustained-release particles are absorbed into the body.

In the case of an oral formulation, unlike the sustained-release particles of the present disclosure, the amount of absorption in the body is relatively low.

According to the administration of the oral formulation, the blood concentration value is higher than that of the sustained-release particles of the present disclosure, but a bioabsorption rate is lower than that of the sustained-release particles of the present disclosure due to the influence of the half-life of the drug.

That is, after administration into the body, the blood concentration is high, but the absorption rate is low due to the short residence time in the body.

On the other hand, the sustained-release particles of the present disclosure may exhibit a drug release effect for a long time while maintaining a relatively low blood concentration value, thus exhibiting excellent bioavailability. Thus, due to these results, it can be said that the administration effect of finasteride is better than that of an oral formulation.

The area under the concentration ($AUC_{0-t}$) of finasteride may be 70 to 100 (μg*h/L) for 1 mg of finasteride administered.

As described above, the area under the concentration curve of finasteride is not affected by the content of finasteride, considering that differences may occur depending on the content of finasteride contained in the injectable composition, and in order to confirm the influence by the sustained-release particles, the value of $AUC_{0-t}$ compared to 1 mg of finasteride was confirmed.

As described above, it can be confirmed that the $AUC_{0-t}$ value for 1 mg of finasteride administered, is 70 to 100 (μg*h/L), which exhibits an excellent effect for finasteride administration, compared to the oral formulation.

The sustained-release particles comprising finasteride of the present disclosure can continuously release finasteride for 1 to 3 months by injection into the body.

The sustained-release particles comprising finasteride of the present disclosure are prepared in the order of: preparing a first mixture (S100); preparing a second mixture (S200); injecting the first mixture into a microchannel in a linear direction (S300); injecting the second mixture into a microchannel on either side or on one side (S400); collecting sustained-release particles (S500); stirring the collected sustained-release particles (S600); and washing and drying the sustained-release particles (S700).

More specifically, a method of preparing sustained-release comprising finasteride according to an embodiment of the present disclosure will be described as follows.

The step S100 which is a step of preparing a first mixture, is a step of preparing a first mixture by dissolving a biodegradable polymer and finasteride in an organic solvent, and the biodegradable polymer is selected from the group consisting of, but is not limited to, polylactic acid, polylactide, polylactic-co-glycolic acid, polylactide-co-glycolide (PLGA), polyphosphazine, polyiminocarbonate, polyphosphoester, polyanhydride, polyorthoester, polycaprolactone, polyhydroxyvalate, polyhydroxybutyrate, polyamino acids, and combinations thereof, and is preferably polylactide-co-glycolide (PLGA).

In addition, the organic solvent is water immiscible and is, but is not limited to, for example, one or more selected from the group consisting of chloroform, chloroethane, dichloroethane, trichloroethane, and a mixture thereof, preferably dichloromethane. The organic solvent is capable of dissolving the biodegradable polymer and finasteride and is not limited thereto, and any organic solvent can be used as long as it can be easily selected by those skilled in the art.

The step S100 is a step of preparing a first mixture by dissolving the biodegradable polymer and finasteride, and an organic solvent as described above is used as a solvent. In the above step, the biodegradable polymer and finasteride are completely dissolved by using the organic solvent using dissolution properties of the biodegradable polymer and finasteride. After the biodegradable polymer and finasteride are completely dissolved, the first mixture comprises the biodegradable polymer and finasteride at a weight ratio of 2:1 to 15:1.

If the weight ratio of the biodegradable polymer and finasteride is less than 2:1, that is, if the biodegradable polymer is included at less than the above weight ratio, the weight ratio of the biodegradable polymer is smaller than that of finasteride, and thus it may be difficult to prepare the sustained-release particles in a form that comprises finasteride evenly distributed in spherical biodegradable polymer particles. If the weight ratio of the biodegradable polymer and finasteride exceeds 15:1, that is, if the biodegradable polymer is included in excess of the above weight ratio, the content of finasteride in the sustained-release particles is small, and thus it may be necessary to administer a large amount of the sustained-release particles in order to administer a desired concentration of the drug.

More specifically, the biodegradable polymer in the first mixture includes in an amount of 10 to 20% by weight, preferably 15% by weight, but the amount is not limited thereto.

In the step S200, which is a step of preparing a second mixture, the second mixture is prepared by dissolving a surfactant in water. As the surfactant, any surfactant may be used without limitation as long as the surfactant can help the biodegradable polymer solution form a stable emulsion. Specifically, the surfactant is one or more selected from the group consisting of nonionic surfactants, anionic surfactants, cationic surfactants, and a mixture thereof, and more specifically one or more selected from the group consisting of methylcellulose, polyvinylpyrrolidone, lecithin, gelatin, polyvinyl alcohol, polyoxyethylene sorbitan fatty acid ester, polyoxyethylene castor oil derivative, sodium lauryl sulfate, sodium stearate, ester amine, linear diamine, patty amine, and a mixture thereof, preferably polyvinyl alcohol, and is not limited thereto.

The steps S300 and S400 are steps of injecting the first mixture and the second mixture into microchannels formed on the wafer and allowing the first mixture and the second mixture to flow therein.

More specifically, the microchannel may be formed on a material selected from the group consisting of a silicon wafer or a polymer film, but examples of the material are not limited thereto, and any material capable of forming a microchannel may be used.

The polymer film may be selected from the group consisting of polyimide, polyethylene, fluorinated ethylene propylene, polypropylene, polyethylene terephthalate, polyethylene naphthalate, polysulfone polysulfone and a mixture thereof, but is not limited thereto.

As an example, aluminum is deposited on a silicon wafer using an e-beam evaporator, and a photoresist is patterned on the aluminum using a photolithography technique. Thereafter, aluminum is etched using the photoresist as a mask, the photoresist is removed, silicon is etched with deep ion reactive etching (DRIE) using aluminum as a mask, and then, glass is anodic bonded onto the wafer to be sealed, after the aluminum is removed, thereby preparing the microchannel.

The microchannel has, but is not limited to, an average diameter of 35 to 55 μm, preferably 50 μm. If the average diameter of the microchannel is 35 μm or less, there is a possibility the sustained-release particles will be prepared as small sustained-release particles having a diameter of 20 μm or less, so that the sustained-release particles are highly likely to being engulfed by macrophages after injection into the human body, thereby affecting the release of effective drugs and the absorption thereof in vivo. In addition, when the size of the prepared sustained-release particles exceeds 55 μm, foreign body sensation and pain may be increased when administered as the injectable agent, and the particle size distribution of the prepared particles may be increased, making it difficult to prepare sustained-release particles having a uniform particle size.

However, the average diameter of the microchannel may be changed depending on the range of the injection pressure. As an example, if the diameter of the channel is 100 μm, the second mixture should be injected at a pressure of 1,000 to 2,000 mbar, and the first mixture may be injected at a pressure of 200 to 400 mbar.

The average diameter of the microchannel is closely related to an average diameter of the particles, but is also closely related to the injection pressure of the first mixture and the second mixture, and is not limited thereto, and may be changed depending on the average diameter of the particles to be prepared, or pressure conditions upon injection.

Figure 8:
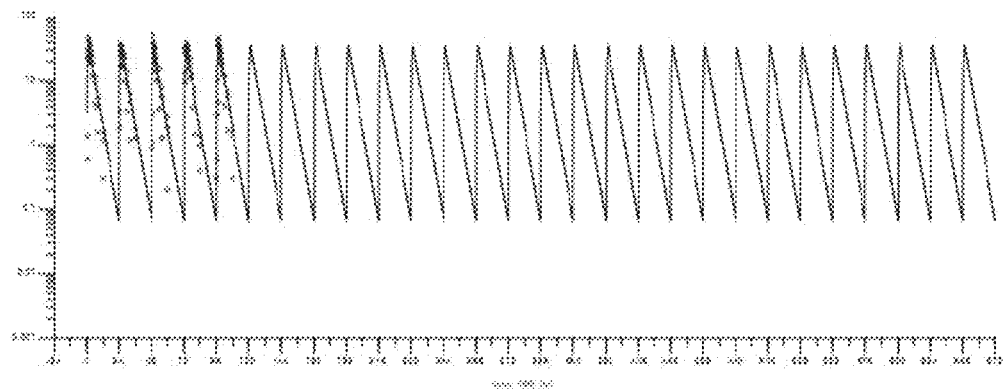
FIG. 8 is a PK profile when the administration is repeated for 28 days in Comparative Example according to an embodiment of the present disclosure.

In addition, a width (w) and a depth (d) of a cross section of the microchannel are closely related to an average diameter (d') of the sustained-release particles to be prepared. As shown in FIG. 8, the ratio of the width (w) of the cross section of the microchannel to the average diameter (d') of the sustained-release particles is in the range of 0.7 to 1.3, and the ratio of the depth (d) of the cross section of the microchannel to the average diameter (d') of the sustained-release particles is in the range of 0.7 to 1.3.

That is, once the average diameter (d') of the sustained-release particles to be prepared is determined, it is possible to prepare sustained-release particles having a desired size only when the ratio of the width (w) and depth (d) of the cross section of the microchannel to the d' is set in the range of 0.7 to 1.3.

The step S300 is a step of injecting the first mixture into a microchannel in a linear direction and allowing the first mixture to flow therein. The step S400 is a step of injecting the second mixture into a microchannel formed on either side or one side so as to form a cross-point with the microchannel in the linear direction and allowing the second mixture to flow therein.

That is, the first mixture flows along the microchannel in the linear direction, and the second mixture flows along the microchannel forming the cross-point with the microchannel in the linear direction on either side or one side with respect to the microchannel in the linear direction and meets the flow of the first mixture At this time, when injected into the microchannel in a linear direction, the first mixture is injected under a constant pressure condition and allowed to flow at a constant flow rate, and at this time, the pressure condition is 500 to 1,500 mbar, preferably 1,100 mbar, but not limited thereto.

In addition, when injected into the microchannel in either side or one side, the second mixture is injected under a constant pressure condition and allowed to flow at a constant flow rate, and at this time, the pressure condition is 1,500 to 2,500 mbar, preferably 2,200 mbar, but not limited thereto.

That is, in order to make the flow of the second mixture forming a cross-point with the flow of the first mixture faster than the first mixture injected into the microchannel in the linear direction, the second mixture is allowed to flow under a higher pressure condition.

As described above, by varying the flow rates of the first mixture and the second mixture, and making the flow rate of the second mixture faster than that of the first mixture, the second mixture having a relatively faster flow rate compresses at the cross-point where the flow of the first mixture meets the flow of the second mixture, and at this time, due to the repulsive force of the first mixture and the second mixture, the biodegradable polymer and finasteride in the first mixture generate spherical sustained-release particles, and more specifically, sustained-release particles in which finasteride is evenly distributed in a spherical biodegradable polymer, are formed.

In the step S500, which is a step of collecting the sustained-release particles, the sustained-release particles are collected in a water bath containing the second mixture, thereby preventing aggregation between the initially generated sustained-release particles.

In the step S500, which is a step of using the second mixture prepared in the step S200, that is, a mixed solution of a surfactant and water, after the second mixture is prepared in the step S200, a part thereof is injected into the microchannel, and the other part thereof is moved to the water bath of the step S500, and is used to prevent aggregation between the collected sustained-release particles.

In the step S600, which is a step of stirring the sustained-release particles collected in the water bath, the sustained-release particles are stirred under a constant temperature condition and at a stirring speed to evaporate and remove the organic solvent present on the surfaces of the sustained-release particles. At this time, the step of stirring the sustained-release particles is performed in the order of: a first stirring step under the stirring conditions of a speed of 150 to 650 rpm for 0.5 to 1.5 hours at 15 to 20° C.; after the first stirring step, a second stirring step under the stirring conditions of a speed of 200 to 1,000 rpm for 2.0 to 6.0 hours at 35 to 45° C.; and after the second stirring step, a third stirring step under the stirring conditions of a speed of 200 to 1,000 rpm for 0.5 to 1.5 hours at 15 to 25° C.

Stirring proceeds at different stirring speed in the first and second stirring steps, and the stirring process is performed using a higher speed in the second stirring process than in the first stirring process.

In addition to the stirring speed, the temperature conditions are also characterized by elevating the temperature in the second stirring process compared to the first stirring process to stir, and as the temperature is increased stepwise, the evaporation rate of the organic solvent present on the surface of the sustained-release particles may be adjusted. That is, by gradually evaporating the organic solvent present on the surface of the sustained-release particles, it is possible to prepare sustained-release particles having a smooth surface.

The temperature at which the first mixture and the second mixture flow through the microchannel is also 15 to 20° C., preferably 17° C. That is, after flowing through the microchannel and forming the cross-point to generate sustained-release particles, the first mixture and the second mixture are kept at a constant low temperature of 15 to 20° C. until the collected sustained-release particles are subjected to the first stirring step. It is possible to prepare and maintain a spherical particle only when a low temperature is maintained during the preparing process of the sustained-release particles. That is, in the case of non-low temperature conditions, it is difficult to prepare particles having a certain spherical shape.

Finally, in the step S700, which is a step of washing and drying the sustained-release particles, the sustained-release particles from which all organic solvents on the surface are removed by stirring are washed several times with purified water that has been sterilized and filtered to remove the surfactant remaining on the sustained-release particles, and then be subjected to freeze-dry.

The finally prepared sustained-release particles have finasteride drugs evenly distributed in the sustained-release particles of spherical biodegradable polymer, and include the biodegradable polymer and finasteride at a weight ratio of 2:1 to 15:1.

The weight ratio of the biodegradable polymer and finasteride included in the sustained-release particles is the same as the weight ratio in the first mixture, and as the sustained-release particles are prepared and all organic solvents are evaporated to remove, it is possible to prepare the sustained-release particles comprising biodegradable polymers and finasteride in the same ratio as the weight ratio in the first mixture.

The injectable composition containing sustained-release particles comprising finasteride according to another embodiment of the present disclosure may include sustained-release particles comprising finasteride; and a suspension solvent.

The injectable composition is in a form in which sustained-release particles are uniformly included in the suspension solvent, and when the injectable composition is administered, the sustained-release particles themselves are injected into the body, thereby exhibiting the effect of long-term administration of finasteride.

More specifically, when the sustained-release particles are injected into the body, finasteride is released by decomposition of the biodegradable polymer, and at this time, the sustained-release particles of the present disclosure are in a form uniformly mixed with the biodegradable polymer and finasteride, thereby exhibiting the effect of administering finasteride at a constant concentration for a long time.

That is, when the injectable composition of the present disclosure is once injected, finasteride is continuously released from the body for 1 to 3 months, thereby solving the problem of having to take the drug every day to increase user convenience.

The suspending solvent comprises an isotonic agent, a suspending agent, and a solvent.

More specifically, the isotonic agent may be selected from the group consisting of D-mannitol, maltitol, sorbitol, lactitol, xylitol, sodium chloride, and a mixture thereof, preferably D-mannitol, but is not limited thereto.

The suspending agent is selected from the group consisting of sodium carboxymethylcellulose, polysorbate 80, starch, starch derivative, polyhydric alcohol, chitosan, chitosan derivative, cellulose, cellulose derivative, collagen (collagen), gelatin, hyaluronic acid (HA), alginic acid, algin, pectin, carrageenan, chondroitin, chondroitin sulfate, dextran, dextran sulfate, polylysine, titin, fibrin, agarose, fluran, xanthan gum, and a mixture thereof, and preferably sodium carboxymethylcellulose and polysorbate 80, but is not limited thereto.

The solvent may use injection water, and any solvent that can be used as injection water may be used without limitation.

Preparation Example 1

Preparation of Subcutaneous Injectable Composition Containing Sustained-Release Particles Comprising Finasteride 1. Preparation of Sustained-Release Particles Comprising Finasteride (Example 1)

A first mixture was prepared by dissolving polylactide-co-glycolide (PLGA) and finasteride in dichloromethane. At this time, the polylactide-co-glycolide in the first mixture is included in a ratio of 15% by weight, and the weight ratio of polylactide-co-glycolide and finasteride is 2:1.

Polyvinyl alcohol, which is a surfactant, was mixed with water to prepare the second mixture containing 0.25% by weight of polyvinyl alcohol.

The first mixture and the second mixture were injected into microchannels formed on a silicone wafer and allowed to flow. At this time, in order for the first mixture and the second mixture to flow at a constant flow rate, the first mixture was allowed to flow under a pressure condition of 1,100 mbar, and the second mixture was allowed to flow under a pressure condition of 2,200 mbar. The temperature condition was maintained at 17° C.

The sustained-release particles generated at the crosspoint where the flow of the first mixture meets the flow of the second mixture were collected in a water bath containing the second mixture. The sustained-release particles collected in the water bath was firstly stirred at 17° C. for 1 hour at a speed of 200 to 400 rpm, and then was secondly stirred for 4 hours at a speed of 300 to 800 rpm with the temperature raised to 43° C., and was thirdly stirred at a speed of 200 to 1,000 rpm for 1 hour at 20° C.

After the stirring was completed, the sustained-release particles were washed several times with purified water filtered through sterilization, and freeze-dried to prepare final sustained-release particles.

Example 2

Example 2 was performed in the same manner as in Example 1, except that the weight ratio of polylactide-co-glycolide and finasteride was 9:1.

Example 3

Example 3 was performed in the same manner as in Example 1, except that the weight ratio of polylactide-co-glycolide and finasteride was 12:1.

2. Preparation of Compositions for Subcutaneous Injection

The sustained-release particles prepared in Examples 1 to 3 were added to 2.0 ml of the suspension solvent based on 1 vial, and then uniformly suspended to prepare subcutaneous injectable compositions.

The suspension solvent was composed of the composition of Table 1 below.

TABLE 1

| Basis of contents | Purpose of mixing | Ingredient name | Amount | Unit |
|---|---|---|---|---|
| 2.0 mL | Isotonic agent | D-Mannitol | 100.0 | mg |
| | Suspending agent | Sodium carboxymethylcellulose | 10.0 | mg |
| | Suspending agent | Polysorbate 80 | 10.0 | mg |
| | Solvent | Injection water | Remainder | |

Experimental Example 1

Examination of Shape of Sustained-Release Particles

In order to examine the shape of the sustained-release particles according to an embodiment of the present disclosure, the shape of the prepared sustained-release particles was examined through an SEM photograph.

Figure 2:
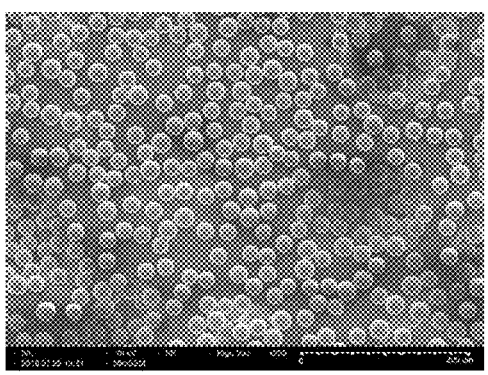
FIG. 2 is an SEM photograph of the sustained-release particles according to an embodiment of the present disclosure.
Figure 3:
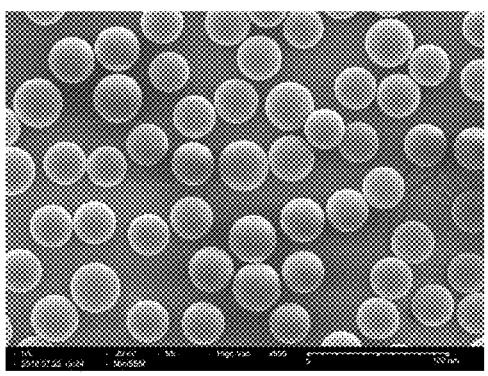
FIG. 3 is an SEM photograph of the sustained-release particles according to an embodiment of the present disclosure.

FIGS. 1 to 3 relate to the SEM photographs of the sustained-release particles according to an embodiment of the present disclosure, from which it can be confirmed that the sustained-release particles of a completely spherical shape are generated.

As a comparative example, unlike the method for preparing the sustained-release particles of the present disclosure, the sustained-release particles were prepared using a solvent evaporation method. Finasteride and the biodegradable polymer were mixed in the same configuration as in Preparation Example 1, and injected into a syringe to prepare particles.

At this time, the stirring was carried out under the conditions of 40° C., 4 hr and 1,000 rpm to prepare particles.

Figure 4:
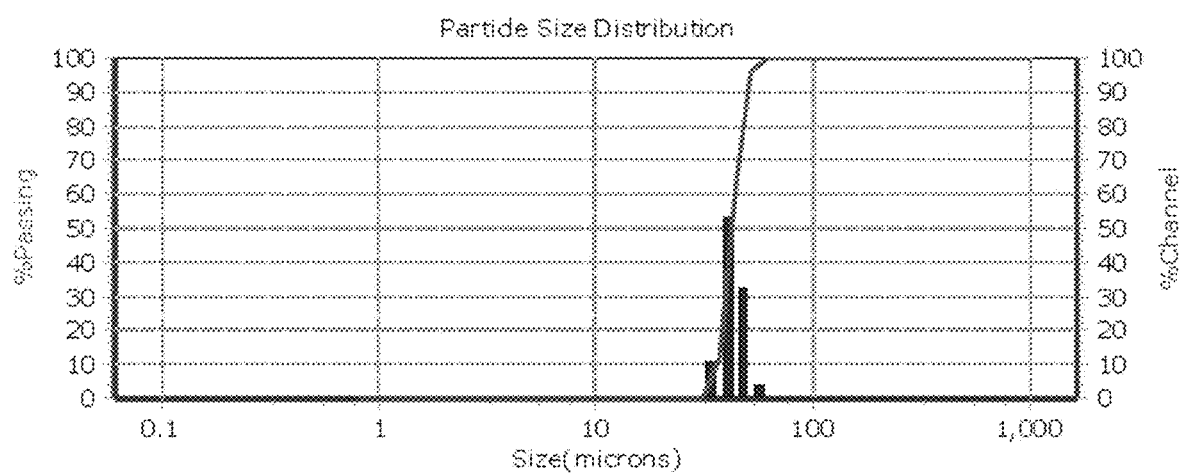
FIG. 4 is a result of measuring the distribution of the sustained-release particles prepared according to an embodiment of the present disclosure.
Figure 5:
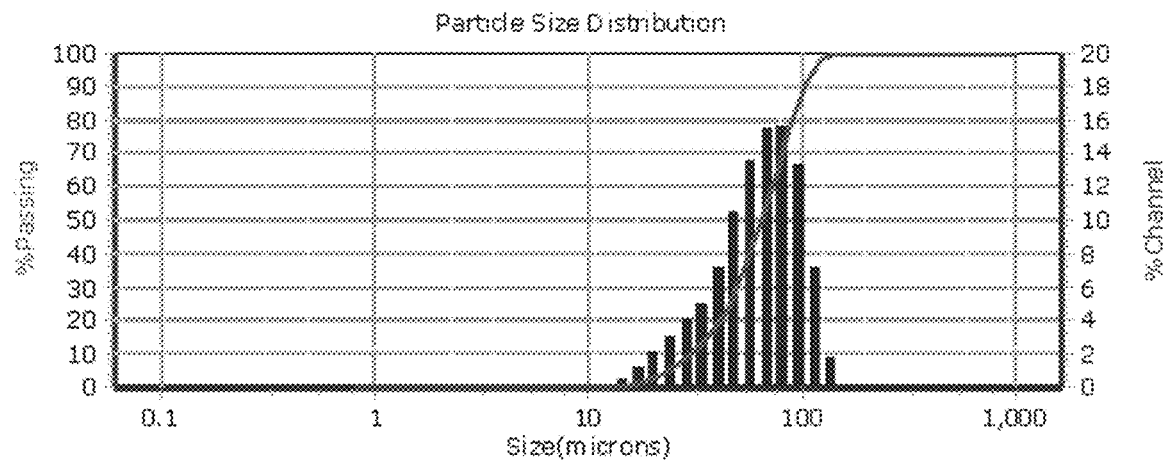
FIG. 5 is a result of measuring the distribution of particles in Comparative Example according to an embodiment of the present disclosure.

The results of measuring the distribution of the sustained-release particles prepared according to Examples 1 to 3 and Comparative Examples are shown in FIGS. 4 and 5.

The results of measuring three times in Examples 1 to 3 are shown in Table 2 below.

TABLE 2

| Example 1. | | Example 2. | | Example 3. | |
|---|---|---|---|---|---|
| % Tile | Size(μm) | % Tile | Size(μm) | % Tile | Size(μm) |
| 10.00 | 36.67 | 10.00 | 37.42 | 10.00 | 37.25 |
| 20.00 | 38.32 | 20.00 | 38.47 | 20.00 | 38.60 |
| 30.00 | 39.62 | 30.00 | 39.35 | 30.00 | 39.71 |
| 40.00 | 40.85 | 40.00 | 40.19 | 40.00 | 40.79 |
| 50.00 | 42.06 | 50.00 | 41.04 | 50.00 | 41.87 |
| 60.00 | 43.41 | 60.00 | 41.89 | 60.00 | 43.07 |
| 70.00 | 45.02 | 70.00 | 42.90 | 70.00 | 44.46 |
| 80.00 | 47.02 | 80.00 | 43.98 | 80.00 | 46.39 |
| 90.00 | 49.71 | 90.00 | 46.31 | 90.00 | 49.20 |
| 95.00 | 57.70 | 95.00 | 48.41 | 95.00 | 51.34 |

The results of measuring a particle diameter are shown in Table 2, and the standard deviations of an average diameter according to the measurement results were identified as 5.10, 3.39 and 4.65, respectively.

It could be confirmed from the measurement results that the sustained-release particles prepared by the preparation method of the present disclosure are prepared as particles of similar size from the results of FIG. 4 and Table 2.

In addition, a specific surface area ($m^2/g$) measured through particle analysis was identified as $1.43 \times 10^{-1}$, $1.46 \times 10^{-1}$ and $1.43 \times 10^{-1}$, respectively.

On the other hand, in the case of Comparative Example, it was confirmed that the particle distribution as shown in Table 3 was shown.

TABLE 3

| Comparative Example | |
|---|---|
| % Tile | Size (μm) |
| 10.00 | 30.05 |
| 20.00 | 41.35 |
| 30.00 | 49.76 |
| 40.00 | 57.17 |
| 50.00 | 64.52 |
| 60.00 | 72.18 |
| 70.00 | 80.53 |
| 80.00 | 90.24 |
| 90.00 | 102.9 |
| 95.00 | 113.0 |

As shown in the experimental results above, it was confirmed that various sizes of the prepared particles existed and the standard deviation was 28.76, which was confirmed for particle distribution through numerical values.

In addition, it was confirmed that the specific surface area ($m^2/g$) of the prepared particles was $1.13 \times 10^1$, indicating a smaller value compared to the particles according to an embodiment of the present disclosure.

Experimental Example 2

Evaluation of Pharmacokinetic Properties

The pharmacokinetic evaluation of the sustained-release particles comprising finasteride of the present disclosure and an injectable formulation containing the same was confirmed.

As Comparative Example, the concentration of finasteride in the blood was quantified using LC-MS/MS after a single administration of oral formulation (Propecia) of 1 mg of finasteride and formulations of Examples 1 to 3 of the present disclosure to beagle dogs.

Pharmacokinetics (PKs) analysis was performed using WinNonlin® software (version 8.0, Pharsight®, Certara™ Company).

The main instruments and devices used in the analysis are as follows.

Figure 6:
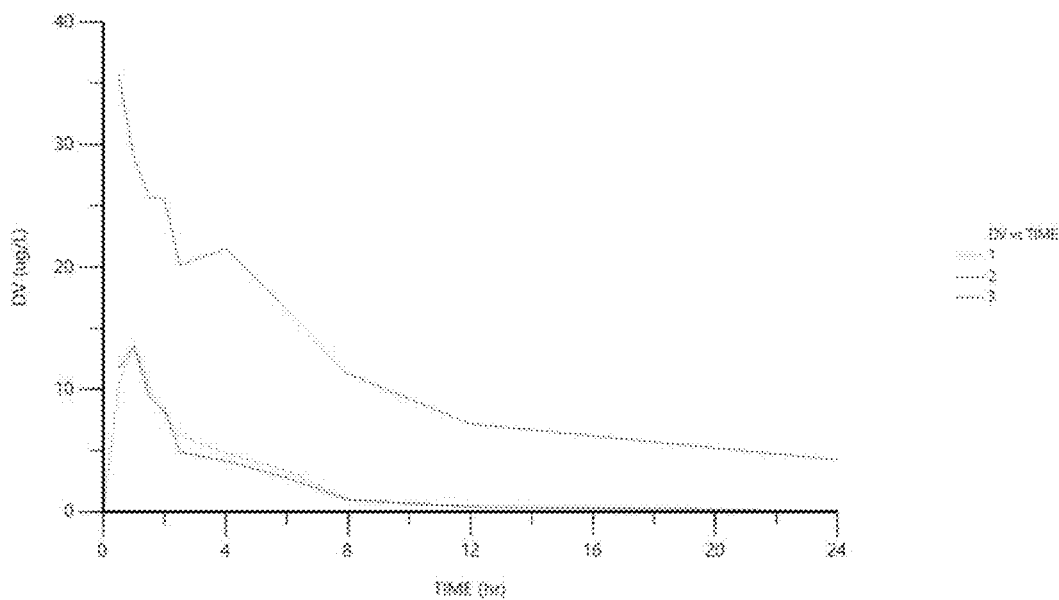
FIG. 6 is a result of measuring PK profile in Comparative Example according to an embodiment of the present disclosure.

Micro balance, SI-234, DENVER INSTRUMENT
Centrifuge, Centrifuge 5424, Eppendorf
Vortex mixer, Model Genie-2, Scientific Industries
Auto pipette, Research plus 20, 100, 200, 1,000 μL, Eppendorf
Screw caps, Microsolve
Vials, Screw top 300 μL, Microsolve
Syringe dispenser, PB-600, HAMILTON COMPANY
Ultrasonic cleaner, 3510E-DTH, BRANSONIC
HPLC, Agilent Technolgies 1290 Infinity II, Agilent
Mass spectrometer, 6490 Triple Quad LC/MS, Agilent Technologies
Data processing system, Masshunter Workstation Ver B.07 (Agilent)
LC-MS/MS conditions are as follows.
Chromatography conditions
HPLC, Agilent Technolgies 1290 Infinity II Agilent Technologies
Column: Phenomenex Kinetex C18, 1.7 μm (100 mm×2.1 mm, I.D.)
Column temperature: 40±0.5° C.
Mobile phase: (A) 0.1% Formic acid in DW (B) 100% Methanol
Isocratic elution mobile phase A:B (40:60, v/v)
Flow rate: 0.2 mL/min
Injection volume: 5 μg
Sample tray temperature: 10±5° C.
Injector wash solution strong: 70% Methanol
Injector wash solution weak: 30% Methanol
Acquisition time: 8 min
Autosampler run time: 8 min
(DW: distilled water)
Mass detector conditions
Mass spectrometer, 6490 Triple Quad LC/MS, Agilent Technologies
Ionization: Positive ion electrospray (ESI+)
Mode: MRM
Gas temperature: 200° C.
Gas flow: 14 L/min
Nebulizer: 20 psi
Capillary: 3000 V The PK profile of the single oral administration of Propecia (ID01-03) is shown in FIG. 5. In addition, the change in blood concentration of finasteride according to time after the single administration of Propecia is as shown in FIG. 6.

The PK parameters of the control drug administration group are as shown in Table 4 below. The pharmacokinetic parameters of each test subject were calculated to determine a blood concentration time-area under the curve (AUC∞), a maximum blood concentration ($C_{max}$), a peak blood concentration arrival time ($T_{max}$), a disappearance half-life (t½), a clearance (CL), and an apparent distribution volume (Vd) using 'WinNonlin® program (ver. 8.0, Pharsight®, a Certara™ Company)'.

$AUC_\infty$ was calculated from the sum of the $AUC_t$ calculated from the plasma concentration until the last measurable blood collection point after administration and the area under the blood concentration-time curve obtained by extrapolating from the last measurable blood collection point to infinity, and $C_{max}$ was calculated as the maximum value among the measured values of the individual's blood concentration, $t_{1/2}$ was calculated as the time it took for the first dose of the drug to become ½, that is, 0.693/k. CL was calculated from the relationship of drug amount/AUC, and Vd was calculated from the relationship of CL/k.

TABLE 4

| ID | Elimination constant | Half-life | Cmax (µg/L) | Vd/F (L) | CL/F (L/hr) | $AUC_{inf}$ (hr*µ/L) | $MRT_{inf}$ (hr) |
|---|---|---|---|---|---|---|---|
| Secondary PK study results | | | | | | | |
| 1 | 0.36 | 1.92 | 46.30 | 17.17 | 6.19 | 161.47 | 4.20 |
| 2 | 0.33 | 2.07 | 37.50 | 17.32 | 5.80 | 172.62 | 4.12 |
| 3 | 0.44 | 1.59 | 44.80 | 20.05 | 8.73 | 114.51 | 2.90 |
| Mean | 0.38 | 1.86 | 42.87 | 18.18 | 6.91 | 149.53 | 3.74 |
| SD | 0.05 | 0.25 | 4.71 | 1.62 | 1.59 | 30.84 | 0.73 |
| Tertiary PK study results | | | | | | | |
| 1 | 0.30 | 2.32 | 13.71 | 69.96 | 20.87 | 47.92 | 3.58 |
| 2 | 0.12 | 5.64 | 35.68 | 29.10 | 3.58 | 279.47 | 8.83 |
| 3 | 0.12 | 5.59 | 13.48 | 171.14 | 21.24 | 47.09 | 4.44 |
| Mean | 0.18 | 4.52 | 20.96 | 90.06 | 15.23 | 124.83 | 5.62 |
| SD | 0.10 | 1.89 | 12.75 | 73.12 | 10.09 | 133.93 | 2.82 |

Figure 7:
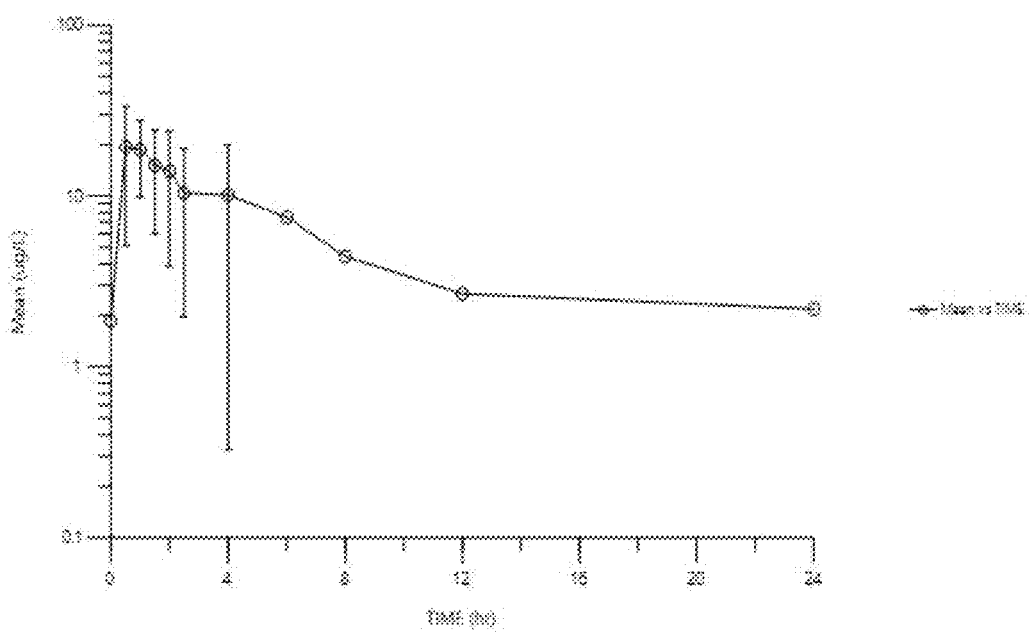
FIG. 7 illustrates a change of blood concentration in Comparative Example according to an embodiment of the present disclosure.

For comparison with the injectable formulation of the present disclosure, a simulation result by setting a 28-day repeated administration scenario based on the results of repeated administration of Propecia 1 mg QD in the PK Study is as shown in FIG. 7.

Figure 9:
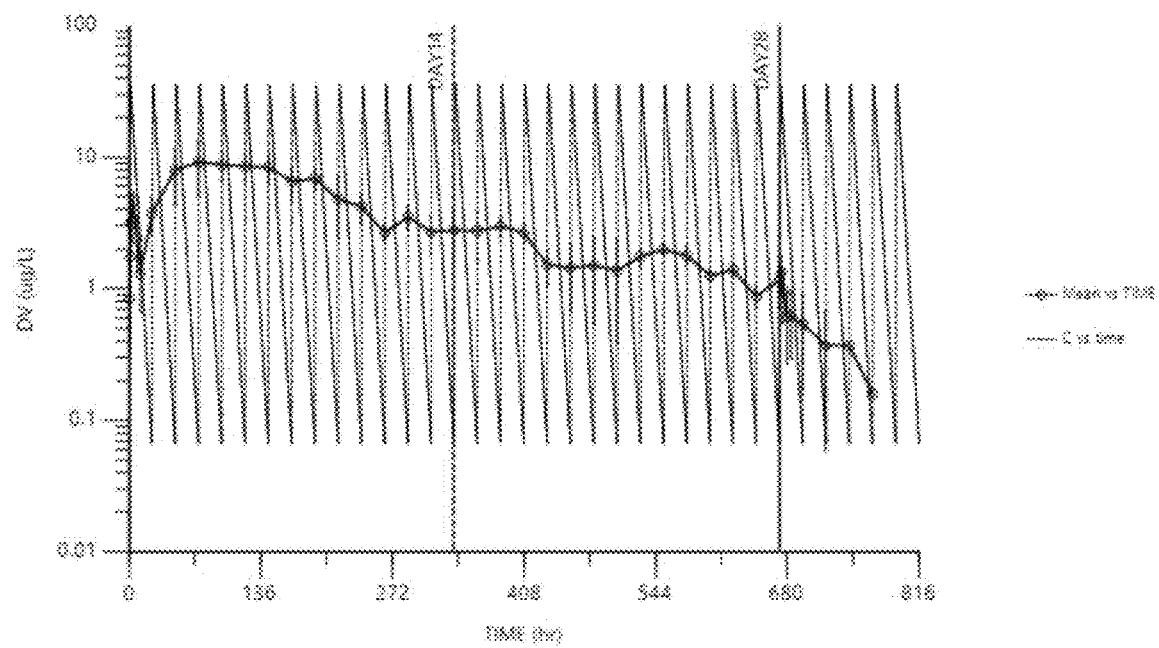
FIG. 9 is a result of measuring an average blood concentration profile of the sustained-release particles according to an embodiment of the present disclosure.
Figure 10:
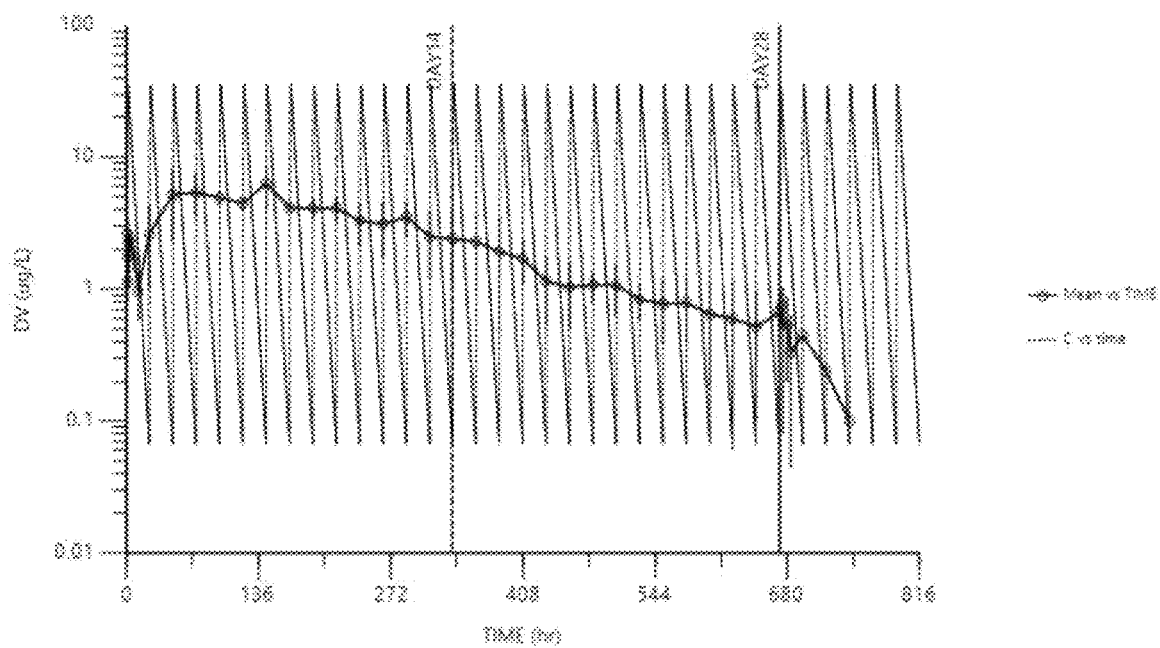
FIG. 10 is a result of measuring an average blood concentration profile of the sustained-release particles according to an embodiment of the present disclosure.
Figure 11:
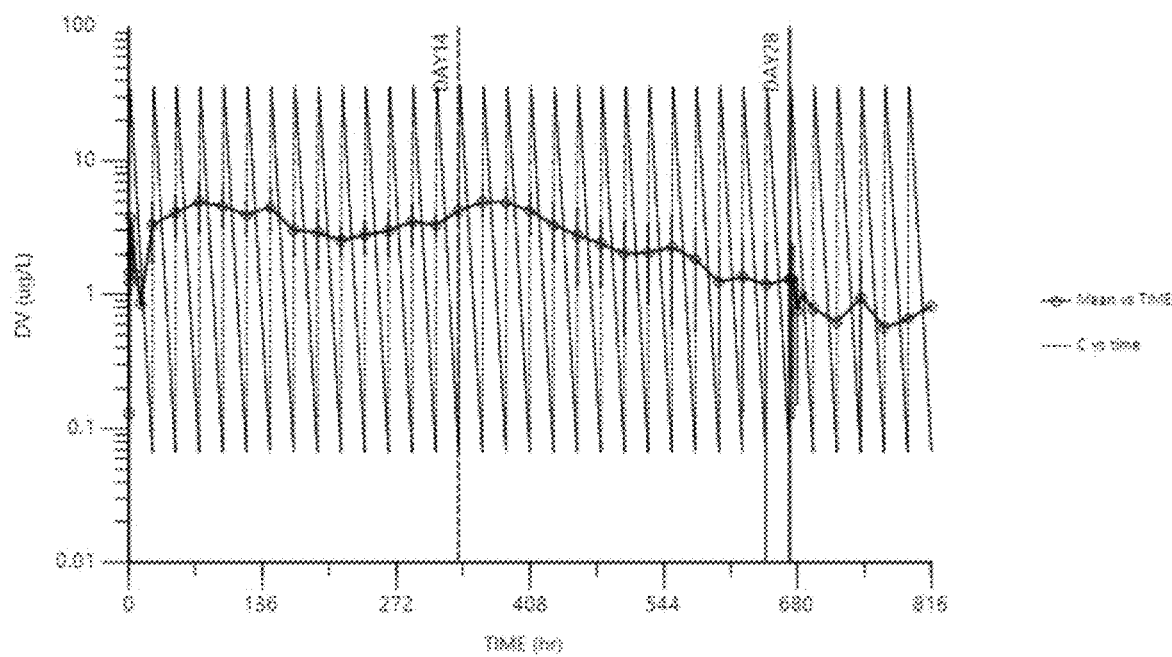
FIG. 11 is a result of measuring an average blood concentration profile of the sustained-release particles according to an embodiment of the present disclosure.

In addition, the results of administering the injections of Examples 1 to 3 of the present disclosure to beagle dogs and confirming the blood concentration profile of finasteride are shown in FIGS. 8 to 10.

Detailed PK profiles are shown in Table 5 below.

TABLE 5

| Group | ID | $AUC_{0-t}$ (µg*h/L) | Average $AUC_{0-t}$ | Standard deviation | $C_{max}$ (µg/L) | Average $C_{max}$ | Standard deviation |
|---|---|---|---|---|---|---|---|
| Example 1 | 6 | 115.63 | 287.76 | 120.85 | 0.30 | 0.94 | 0.73 |
| | 7 | 303.72 | | | 0.71 | | |
| | 8 | 298.14 | | | 0.75 | | |
| | 9 | 456.68 | | | 2.20 | | |
| | 10 | 287.76 | | | 0.74 | | |
| Example 2 | 11 | 1199.92 | 879.29 | 284.88 | 3.36 | 2.67 | 0.65 |
| | 12 | 470.86 | | | 1.97 | | |
| | 13 | 773.85 | | | 2.68 | | |
| | 14 | 863.59 | | | 2.08 | | |
| | 15 | 1088.22 | | | 3.27 | | |
| Example 3 | 16 | 2496.27 | 1932.90 | 562.37 | 3.27 | 5.32 | 3.12 |
| | 17 | 1793.04 | | | 6.16 | | |
| | 18 | 1068.56 | | | 2.58 | | |
| | 19 | 1948.54 | | | 4.23 | | |
| | 20 | 2358.08 | | | 10.35 | | |

It could be confirmed that according to the measurement results of the PK profile for the Comparative Examples and Examples 1 to 3, in the case of the oral formulation, the maximum blood concentration value of finasteride was greater than that of Examples 1 to 3, but $AUC_{0-t}$ indicated a small value.

In addition, it could be confirmed that as for whether or not the drug efficacy persists for 28 days, Comparative Example 1 should be taken every day to maintain an effective blood concentration capable of maintaining the drug effect, while in Preparation Examples 1 to 3 of the present disclosure, the drug efficacy lasts for twenty eight (28) days, while maintaining the effective blood concentration.

Preparation Example 2

Preparation of Subcutaneous Injectable Composition Containing Sustained-Release Particles Comprising Finasteride After preparing the sustained-release particles in the same manner as in Preparation Example 1, the subcutaneous injectable composition was prepared.

At this time, the sustained-release particles were prepared to include the finasteride with 10% (Example 1), 20% (Example 2), 40% (Example 3), 60% (Example 4) and 100% (Example 5) based on 1 vial.

Experimental Example 3

Evaluation of pharmacokinetic properties using sustained-release particles prepared in Preparation Example 2

Examples 1 to 3 prepared in Preparation Example 2 are the same as the previous pharmacokinetic evaluation experiment, and the results of adding the results for Examples 4 and 5 are shown in Table 6 below.

TABLE 6

| | ID | AUC$_{0-t}$ (hr*μ/L) | Mean | SD | Cmax (μg/L) | Mean | SD |
|---|---|---|---|---|---|---|---|
| Example 1 | 6 | 115.63 | 287.76 | 120.85 | 0.30 | 0.94 | 0.73 |
| | 7 | 303.72 | | | 0.71 | | |
| | 8 | 298.14 | | | 0.75 | | |
| | 9 | 456.68 | | | 2.20 | | |
| | 10 | 287.76 | | | 0.74 | | |
| Example 2 | 11 | 1199.92 | 879.29 | 284.88 | 3.36 | 2.67 | 0.65 |
| | 12 | 470.86 | | | 1.97 | | |
| | 13 | 773.85 | | | 2.68 | | |
| | 14 | 863.59 | | | 2.08 | | |
| | 15 | 1088.22 | | | 3.27 | | |
| Example 3 | 16 | 2496.27 | 1932.90 | 562.37 | 3.27 | 5.32 | 3.12 |
| | 17 | 1793.04 | | | 6.16 | | |
| | 18 | 1068.56 | | | 2.58 | | |
| | 19 | 1948.54 | | | 4.23 | | |
| | 20 | 2358.08 | | | 10.35 | | |
| Example 4 | 21 | 1536.69 | 1925.434 | 493.3951 | 3.89 | 5.08 | 1.61 |
| | 22 | 1384.29 | | | 3.08 | | |
| | 23 | 1854.88 | | | 5.79 | | |
| | 24 | 2315.22 | | | 5.47 | | |
| | 25 | 2536.08 | | | 7.17 | | |
| Example 5 | 26 | 2054.26 | 3346.486 | 1164.368 | 5.25 | 9.45 | 4.51 |
| | 27 | 2532.32 | | | 6.20 | | |
| | 28 | 4100.60 | | | 16.19 | | |
| | 29 | 4919.09 | | | 11.76 | | |
| | 30 | 3126.18 | | | 7.85 | | |

Figure 12:
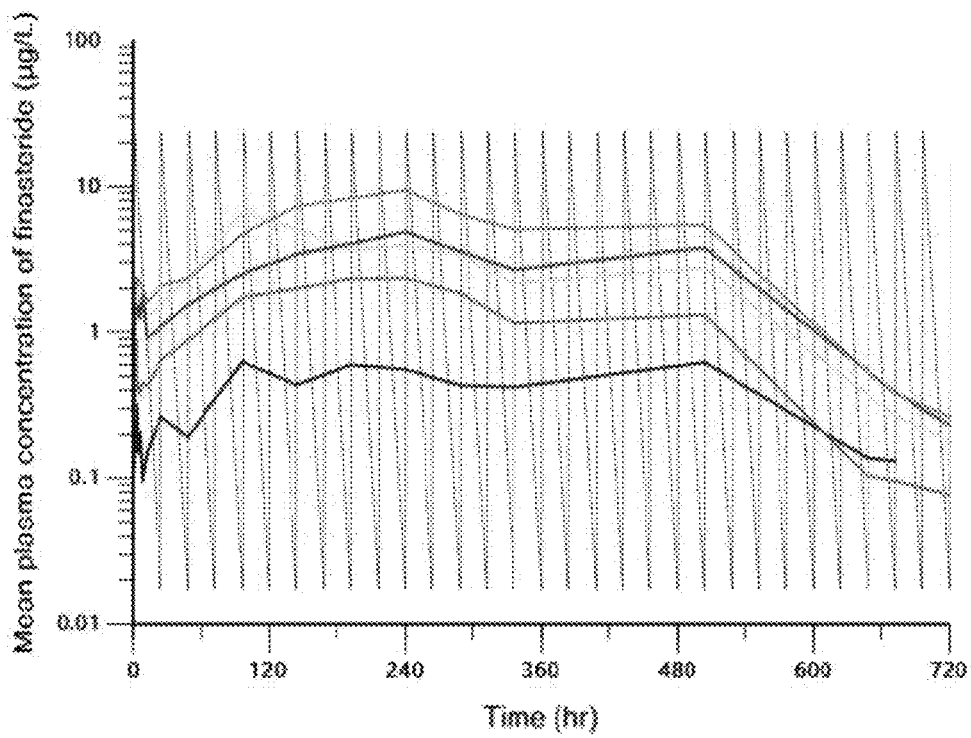
FIG. 12 is a result of measuring an average blood concentration profile of the sustained-release particles depending on the content of finasteride of an injectable composition according to an embodiment of the present disclosure.

The results are values for AUC$_{0-t}$ and C$_{max}$, and the effect of sustained drug release for 1 month is as shown in FIG. 12.

In FIG. 12, the value of blood drug concentration is as follows: a blue graph is for Example 1, an orange graph is for Example 2, a yellow graph is for Example 3, a pink graph is for Example 4, and a green graph is for Example 5.

It could be confirmed from FIG. 12 that the difference in the blood concentration value occurs due to the difference in the content of finasteride contained in the administered injectable composition, but the profile of the drug concentration did not cause an initial over-release problem, and finasteride was continuously released for 1 month.

In addition, the effect of preventing hair loss and treating benign prostatic hyperplasia due to the release of finasteride can be confirmed based on the effect of inhibiting DHT production.

The effect of inhibiting the DHT production was measured by measuring the rate of change in concentration (%) based on 100% of the average blood DHT concentration of the beagle dog before the experiment proceeds.

Figure 13:
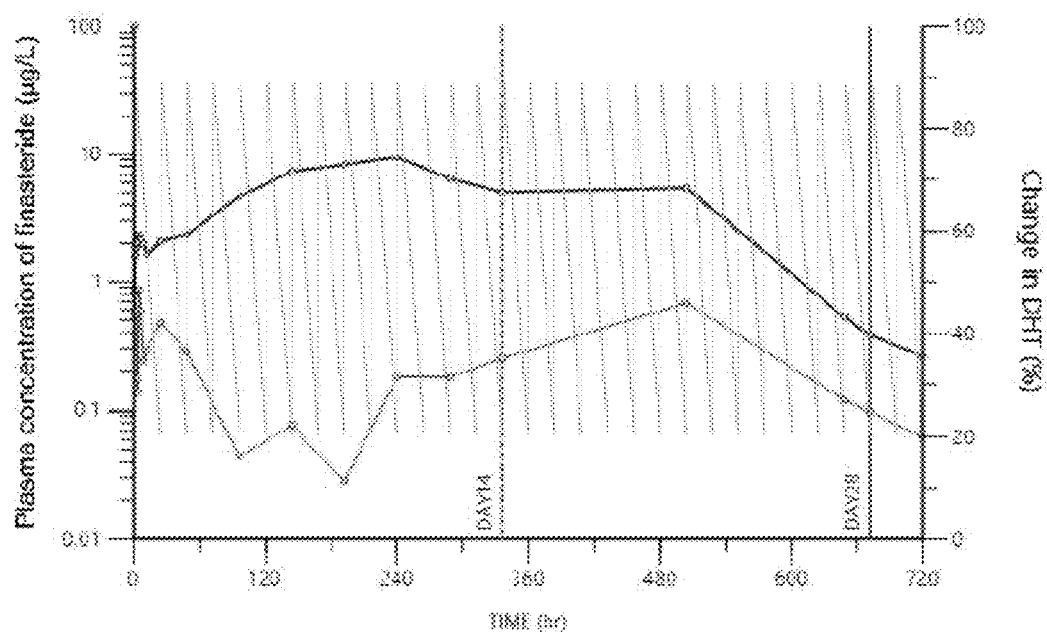
FIG. 13 is a result of measuring an average blood concentration profile of finasteride and a rate of change in DHT after administration of an injectable composition according to an embodiment of the present disclosure.

The relevant experimental results are as shown in FIG. 13.

FIG. 13 illustrates the blood drug concentration and inhibition of the DHT production for 1 month of Example 5, and it can be confirmed that the effect of inhibiting the DHT production appears due to the continuous release of finasteride for 1 month.

Figure 14:
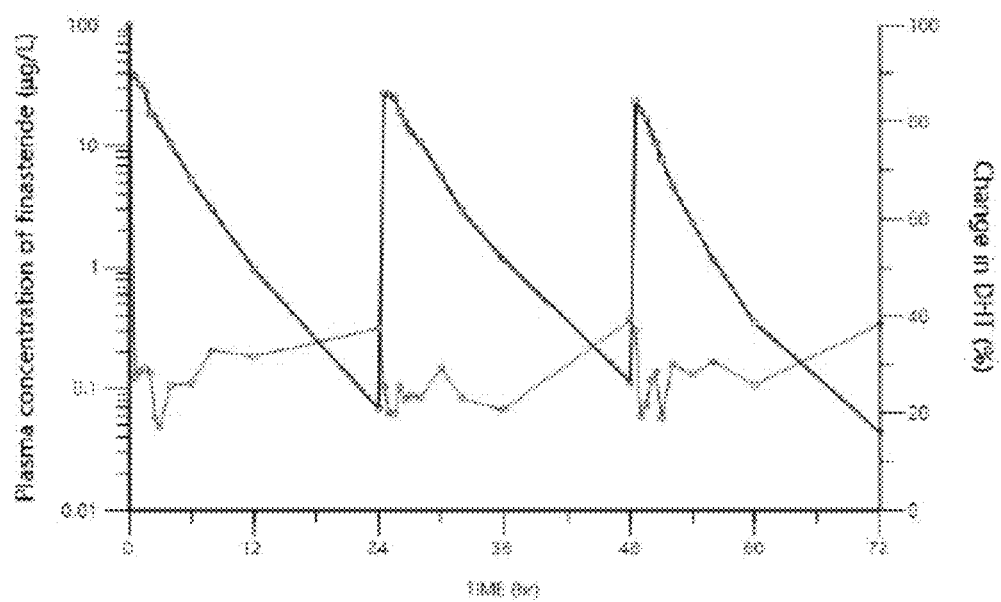
FIG. 14 is a result of measuring a blood concentration profile and a rate of change in DHT in an oral formulation according to an embodiment of the present disclosure.

FIG. 14 is a result of measuring a blood drug concentration value and an effect of inhibiting the DHT production according to repeated administration of 1 mg of Propecia Q.D.

According to the experimental results above, it can be confirmed that the oral formulation has an initial over-release when administered, and then exhibits a DHT inhibitory effect, but the blood drug concentration drops rapidly over time, and accordingly, the DHT inhibitory effect disappears. Thus, there is a hassle of having to be administered orally repeatedly every day.

Figure 15:
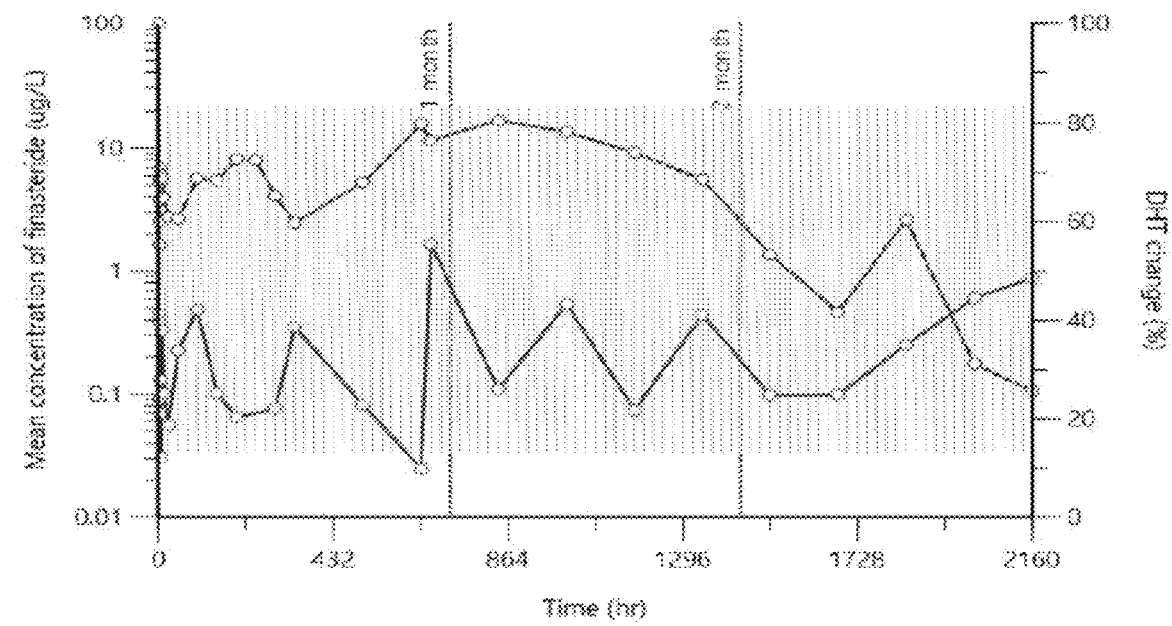
FIG. 15 is a result of measuring an average blood concentration profile of finasteride and a rate of change in DHT for 3 months after administration of an injectable composition according to an embodiment of the present disclosure.

FIG. 15 illustrates whether the drug is continuously released for 3 months after administering the sustained-release particle of the present disclosure. It could be confirmed from FIG. 15 that a certain degree of the drug was released without over-release of finasteride for 3 months, and it was conformed from FIG. 15 that the effect of inhibiting the generation of DHT was also maintained.

Although the preferred embodiments of the present disclosures have been described in detail above, the scope of the present disclosure is not limited thereto, and various modifications and improvements made by those skilled in the art using the basic concept of the present disclosure defined through the following claims also belong to the scope of rights of the present disclosure.

The invention claimed is:

1. A sustained-release injectable composition comprising finasteride,
    wherein the sustained-release injectable composition injected into a body continuously releases finasteride,
    the released finasteride has a ratio of a maximum blood concentration ($C_{max}$) to an initial blood concentration ($C_{int}$) of 2 to 11, and
    the sustained-release injectable composition includes sustained-release particles, wherein a biodegradable polymer and the finasteride are evenly distributed in the sustained-release particles, the sustained-release particles have an average diameter of 35 to 55 μm, and a standard deviation of the average diameter is 3.0 to 5.5 μm.

2. The composition of claim 1, wherein the maximum blood concentration ($C_{max}$) of finasteride is 0.3 to 0.5 μg/L for 1 mg of finasteride administered.

3. The composition of claim 1, wherein an area under the concentration curve (AUC$_{0-t}$) of finasteride is 70 to 100 (μg*h/L) for 1 mg of finasteride administered.

4. The composition of claim 1, wherein the sustained-release injectable composition has no initial over-release problem due to the controlled release rate of the drug, forms a continuous release pattern for 1 to 3 months, and inhibits the production of DHT and testosterone.

5. The composition of claim 1, wherein the injectable composition includes a suspension solvent, and the suspension solvent includes an isotonic agent, a suspending agent and a solvent.

6. The composition of claim 5, wherein the isotonic agent is selected from the group consisting of D-mannitol, maltitol, sorbitol, lactitol, xylitol, sodium chloride and a mixture thereof.

7. The composition of claim 5, wherein the suspending agent is selected from the group consisting of sodium carboxymethylcellulose, polysorbate 80, starch, starch derivatives, polyalcohol, chitosan, chitosan derivative, cellulose, cellulose derivatives, collagen, gelatin, hyaluronic acid (HA), alginic acid, algin, pectin, carrageenan, chondroitin, chondroitin sulfate, dextran, dextran sulfate, polylysine, titin, fibrin, agarose, fluran, xanthan gum and a mixture thereof.

* * * * *